(12) United States Patent
Nelson et al.

(10) Patent No.: US 6,285,198 B1
(45) Date of Patent: Sep. 4, 2001

(54) GRAIN MOISTURE SENSOR

(75) Inventors: Frederick William Nelson, Moline; Kent Robert Hawk, Erie; Wayne Farrior Smith, Moline, all of IL (US); Terence Daniel Pickett, Bluegrass, IA (US)

(73) Assignee: Deere & Company, Moline, IL (US)

( * ) Notice: Subject to any disclaimer, the term of this patent is extended or adjusted under 35 U.S.C. 154(b) by 952 days.

(21) Appl. No.: 08/888,354

(22) Filed: Jul. 3, 1997

Related U.S. Application Data

(63) Continuation of application No. 08/522,884, filed on Sep. 1, 1995, now abandoned.

(51) Int. Cl.[7] ............................ G01R 27/26; G01F 23/26; A01D 75/28
(52) U.S. Cl. ...................... 324/664; 324/658; 73/335.04; 56/10.213
(58) Field of Search ...................... 56/10.2 B; 73/335.03, 73/29.01, 335.04; 324/664, 665, 658, 670, 669

(56) References Cited

U.S. PATENT DOCUMENTS

| | | | |
|---|---|---|---|
| 2,665,409 | * 1/1954 | Rogers | 324/689 |
| 2,788,487 | * 4/1957 | Grogg | 324/689 |
| 3,482,162 | * 12/1969 | Wochnowski | 324/689 |
| 3,760,267 | * 9/1973 | Williams | 324/689 |
| 4,547,725 | * 10/1985 | Oetiker | 324/665 |
| 4,853,614 | * 8/1989 | Carver | 324/689 |
| 5,343,761 | 9/1994 | Myers . | |
| 5,616,851 | * 4/1997 | McMahon | 73/29.01 |

FOREIGN PATENT DOCUMENTS 2087704   6/1982   (GB) .

* cited by examiner

*Primary Examiner*—Safet Metjahic
*Assistant Examiner*—Anjan K. Deb

(57) ABSTRACT

A moisture sensor for an agricultural combine comprises a chamber having an inlet and an outlet and a paddle wheel flow controller located adjacent to the outlet. The paddle wheel flow controller is rotated by an electric motor which is controlled by an electronic controller. Grain from the clean grain elevator is directed through the inlet of the chamber past a capacitance sensor comprising a first, second and third plates. By measuring the capacitance of the grain, the moisture in the grain can be determined.

7 Claims, 2 Drawing Sheets

GRAIN MOISTURE SENSOR

This application is a Continuation of application Ser. No. 08/522,884, filed Sep. 1, 1995 now abandoned.

BACKGROUND OF THE INVENTION

1. Field of the Invention

The invention is directed to a grain moisture sensor that is particularly well adapted for use on an agricultural combine.

2. Description of the Prior Art

Precision farming uses Global Positioning Satellites (GPS) to determine the exact location of a agricultural machine in the field. The machine is fitted with a receiver for receiving radio wave signals from the positioning satellites and converting these signals into position data. Other machine mounted sensors are used to detect crop conditions, such as crop moisture and yield. By combining this information the farmer is able to generate detailed maps of field conditions. The farmer can then take these maps and better control inputs, such as seed, fertilizer and other chemicals.

In yield mapping the farmer maps the output or yield of the field. Typically an agricultural combine would be mounted to a GPS receiver and a mass flow sensor. The mass flow data is combined with the GPS data to form a yield map. Impact type mass flow sensors are sensitive to grain moisture content. Moisture content affects grain weight and this variable must be accounted for in accurately determining mass flow. U.S. Pat. No. 5,343,761 discloses a combine mounted mass flow sensor having capacitance type moisture sensor.

SUMMARY

It is one of the objects of the present invention to provide a moisture sensor having a larger measurement plate area and sample volume than traditional moisture sensors.

It is another object of the present invention to provide a moisture sensor having a very consistent grain sample for each measurement.

It is feature of the present invention that the sensor is mounted to the clean grain elevator. This mounting location reduces the time delay between grain cutting and moisture measurement.

The moisture sensor comprises a vertical chamber having an inlet and an outlet. The chamber is mounted to the clean grain elevator. The chamber is defined by a first wall adjacent and parallel to the clean grain elevator and a second wall spaced from and parallel to the first wall. The first and second walls are joined by two sidewalls. The bottom of the chamber is provided with a paddle wheel which forms a flow control means for retaining clean grain in the chamber. The paddle wheel is rotated by an electric motor. Three conductive plates are positioned between the inlet and the paddle wheel and form a capacitance moisture sensing means. The first and second plates are parallel and adjacent to the first and second walls. The first and second plates are electrically coupled to one another by a jumper. The jumper is formed from the sheet metal of the first and second plates. The third plate is located between the first and second plates. It is positioned in the middle of the chamber between the first and second plates.

The clean grain passing between the first and third, and second and third plates forms a dielectric material. The conductivity of the grain and thereby the capacitance of the sensor is directly related to the moisture content of the grain.

The moisture sensor is provided with an electronic controller. The electronic controller controls the operation of the electric motor driving the paddle wheel. The electric motor ensures there is an adequate supply of grain in the chamber for moisture readings.

A photoelectric emitter and a photoelectric sensor are mounted to the chamber for detecting the supply of grain in the chamber. More specifically, the emitter and sensor are positioned near the top of the chamber and the emitter projects a beam across the chamber where it is reflected back to the sensor by a reflective surface. When the sensor does not detect the beam, grain is blocking the beam and an adequate supply of grain is present in the chamber. Therefore the motor is operated and the paddle wheel turned removing some of the grain out the bottom of the chamber. If the sensor detects the beam, the electric motor is stopped causing clean grain to back up in the chamber.

The combine maybe provided with an additional sensor which detects of the separator is being operated. For example, if the operator shuts off the separator the speed of the separator decreases and this speed drop can be detected. In such a situation the electronic controller drives the electric motor for approximately 20 seconds to evacuate grain from the chamber. In this situation the electronic controller assumes the combine is no longer processing grain and the remaining grain in the chamber is directed to the clean grain elevator and from there into the grain tank.

DETAILED DESCRIPTION

Figure 1:
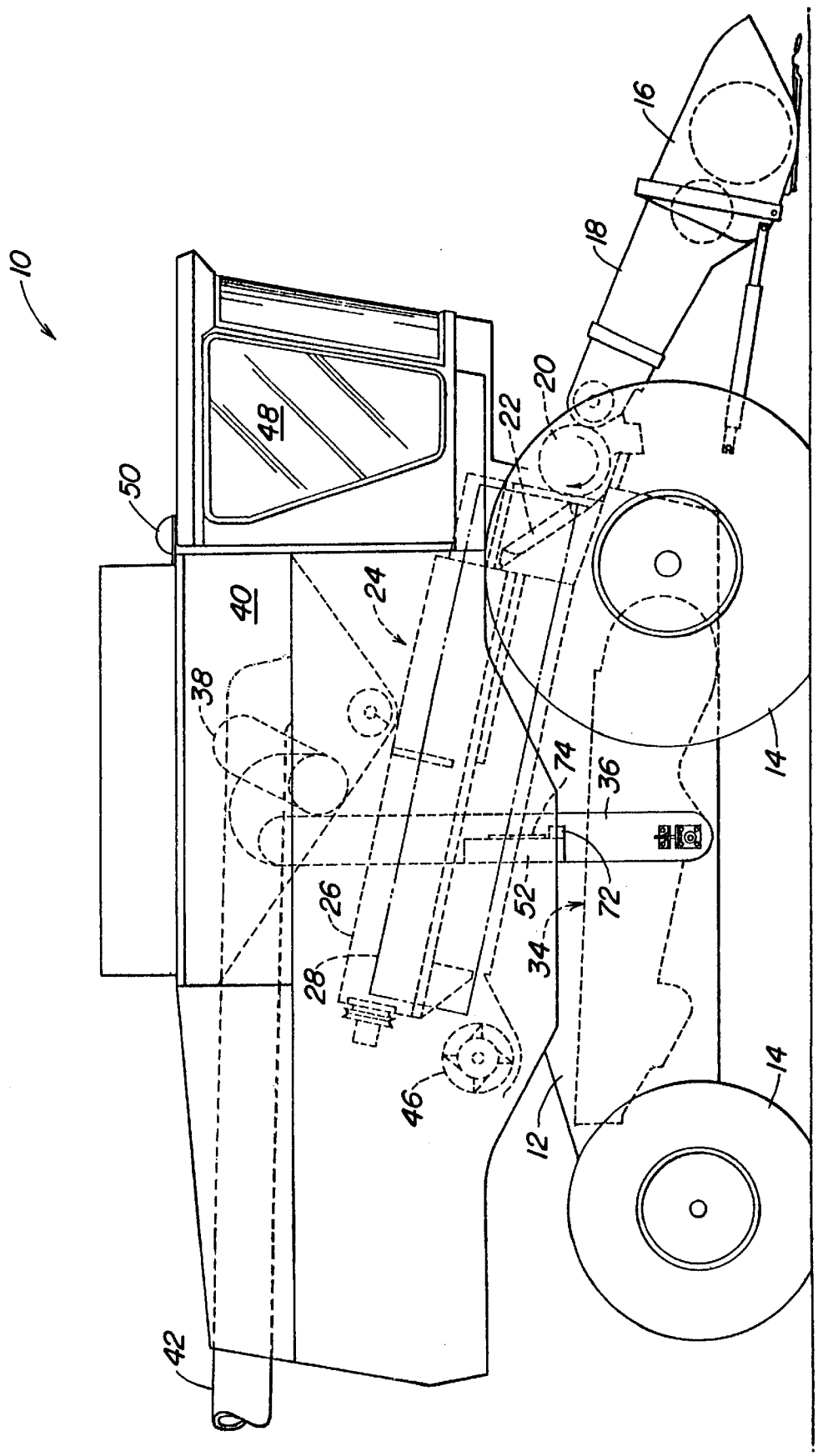
FIG. 1 is a side view of a rotary agricultural combine.

FIG. 1 shows an agricultural combine 10, also known as a combine thresher, comprising a supporting structure 12 having ground engaging means 14 extending from the supporting structure. A harvesting platform 16 is used for harvesting a crop and directing it to a feederhouse 18. The harvested crop is directed by the feederhouse 18 to a beater 20. The beater directs the crop upwardly through an inlet transition section 22 to the axial crop processing unit 24. The axial crop processing unit is located between the sidesheets of the combine. The sidesheets form part of the supporting structure. Although the invention is being described as being mounted on a rotary combine, it may also be used on other combines having a clean grain elevator, such as conventional straw walker machines.

The axial crop processing unit 24 comprises an axial rotor housing 26 and an axial rotor 28 located in the housing. The harvested crop enters the housing through the inlet transition section 22. The rotor is provided with an infeed portion, a threshing portion and a separating portion. The rotor housing has a corresponding infeed section, a threshing section and a separating section.

Both crop processing portions, the threshing portion and the separating portion, are provided with crop engaging assemblies. The threshing section of the rotor housing is provided with a concave and the separating section is provided with a grate. Grain and chaff released from the crop mat falls through the concave and the grate. The concave and grate prevent the passage of crop material larger than grain or chaff from entering the cleaning system 34.

As illustrated in FIG. 1, grain and chaff falling through the concave and grate is directed to cleaning system 34 which removes the chaff from the grain. The clean grain is then directed by a clean grain elevator 36 to a fountain auger 38. The fountain auger 38 directs the grain into grain tank 40. The clean grain elevator and the fountain auger 38 comprise a means for moving the clean grain from the grain floor of the combine to a storage bin formed by grain tank 40. The grain is removed from the grain tank 40 by unloading auger 42. As the straw reaches the end of the crop processing unit it is expelled through an outlet to a beater 46. The beater propels the straw out the rear of the combine. The operation of the combine is controlled from operator's cab 48. A radio receiver 50 for receiving GPS signals is positioned over the operator's cab.

Figure 2:
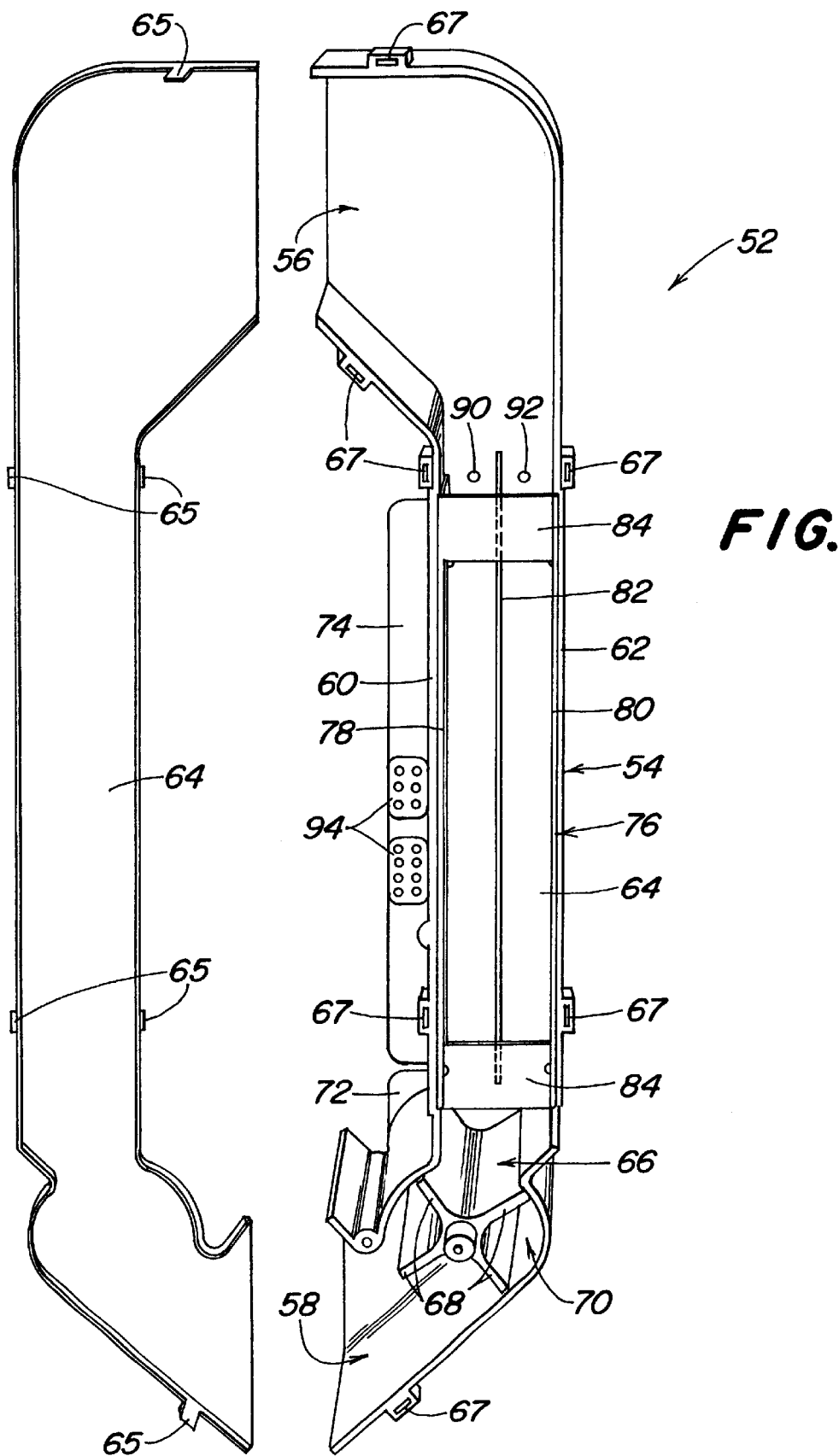
FIG. 2 is a cross sectional side view of the moisture sensor.

As illustrated in FIG. 1, the clean grain elevator 36 is mounted to the right hand side sheet of the supporting structure 12 and as such forms an external wall of the combine. A moisture sensor 52 is mounted ex-situ to the external wall of the clean grain elevator 36. The moisture sensor comprises a vertical chamber 54 having an inlet 56 for receiving clean grain through an inlet formed in the external wall of the clean grain elevator 36 and an outlet 58 for inserting grain back through an outlet formed in the external wall of the clean grain elevator. The vertical chamber comprising a grain moisture analyzer having means for bypassing a portion of the clean grain in the clean grain elevator through the vertical chamber. The chamber itself has a first wall 60 that is adjacent and parallel to the clean grain elevator 36. Parallel to and spaced from the first wall is a second wall 62. Sidewalls 64 join the first and second walls. The chamber is formed from a non-conductor such as plastic. One of the sidewalls maybe detachably mounted to the first and second walls. For example, the chamber illustrated in FIG. 2 has a sidewall removed. The detachable sidewall maybe secured to the rest of the chamber by molded in latches 65 which engage receiving slots 67.

A flow control means or feed means comprising paddle wheel 66 is located just upstream from the outlet 58. The paddle wheel has four flexible rubber paddles 68 that extend across the chamber between the sidewalls for controlling the flow of grain out of the chamber. A cylindrical area 70 is molded inside the chamber for accommodating the paddle wheel. The paddle wheel 66 is rotated by electric motor 72. The electric motor 72 is provided with suitable gearing for slowing its output. The motor is driven by electronic controller 74. The paddle wheel controls the flow of grain through the chamber so that there is an adequate sample of grain to sense grain moisture.

The chamber is also provided with a capacitance sensing means sensing cell 76 which comprises a first, second and third metal plates 78, 80 and 82, respectively. The first two metal plates 78 and 80 are adjacent and parallel to the first and second walls 60 and 62. The first and second plates are electrically coupled to one another by jumpers 84. The first and second plates 78 and 80, and the jumpers 84 are formed from a single piece of sheet metal that is bent in a U-shape. The legs of the U form the first and second plates whereas the jumpers are formed by metal strips extending between the first and second plates. The third plate 82 is parallel to the first two plates and positioned between them. All the plates are coupled to the electrical controller through ports in the side wall 64 of the chamber. Clean grain flowing between the plates forms a dielectric material which varies the capacitance of the system as moisture content varies in the grain. The electronic controller monitors the change in capacitance and relates this to grain moisture by utilizing various capacitance/grain moisture calibration curves that can be derived experimentally for various grains.

To insure an adequate sample of grain for the moisture sensor 52, electronic controllers provided with a photoelectric emitter and a photoelectric sensor 90 and 92 which measure grain level in the chamber. The photoelectric emitter emits a beam which is reflected from a reflective surface formed by top jumper 84, which is detected by photoelectric sensor 92. If the jumper is not reflective, a reflective tape may be mounted to the inside surface of the jumper. In response to signals from the photoelectric sensor 92, the electronic controller controls the rotation of paddle wheel 66. More specifically, if grain is present in the upper reaches of the chamber, the photoelectric sensor will not receive a signal from the photoelectric emitter, and the electronic controller will know that the chamber has an adequate sample of grain for measuring grain moisture. Therefore, the electronic controller will energize the electric motor and rotate the paddle wheel. If grain is no longer in the upper reaches of the chamber, and the beam from the photoelectric emitter is detected by the photoelectric sensor, then the electronic controller knows to stop the electric motor, which in turn stops the rotation of the paddle wheel. Grain is then allowed to build up until it again covers the emitter/sensor indicating an adequate size sample.

The electronic controller is also provided with various electrical plugs and connections 94 for connecting the controller to a power supply and also to couple the electronic controller to monitors and other sensors so that its output can be integrated into a precision farming system.

The invention should not be limited to the above described embodiment but should be limited solely to the claims that follow.

What is claimed is:

1. A moisture sensor for an agricultural combine having a clean grain elevator, the moisture sensor comprising:

a vertically extending chamber mounted to the clean grain elevator, the chamber having an upper inlet and a lower outlet, clean grain enters the chamber from the clean grain elevator through the inlet and exits the chamber back into the clean grain elevator through the outlet;

a capacitance sensing means is positioned in the chamber between the outlet and the inlet, the capacitance sensing means senses the capacitance of clean grain in the chamber and provides a capacitance signal that can be related to grain moisture;

a flow control means for controlling the flow of clean grain through the chamber.

2. A moisture sensor as defined by claim 1 wherein the flow control means is located between the capacitance sensing means and the outlet.

3. A moisture sensor as defined by claim 2 wherein the chamber is provided with a first wall adjacent and parallel to the clean grain elevator and a second wall spaced from and parallel to the first wall, two sidewalls extend between the first and second walls.

4. A moisture sensor as defined by claim 3 wherein the flow control means comprises a paddle wheel that is operatively coupled to an electric motor for rotating the paddle wheel.

5. A moisture sensor as defined by claim 4 further comprising an electronic controller for controlling the electric motor, the electronic controller being electrically coupled to the electric motor.

6. A moisture sensor for an agricultural combine having a clean grain elevator, the moisture sensor comprising:

a vertically extending chamber mounted to the clean grain elevator, the chamber having an upper inlet and a lower outlet, clean grain enters the chamber from the clean grain elevator through the inlet and exits the chamber back into the clean grain elevator through the outlet;

a capacitance sensing means is positioned in the chamber between the outlet and the inlet, the capacitance sensing means continually senses the capacitance of clean grain in the chamber and provides a capacitance signal that can be related to grain moisture;

a flow control means for continuously controlling the flow of clean grain through the chamber, the flow control means is located between the capacitance sensing means and the outlet, so that the capacitance sensing means is continually sensing the capacitance of a new clean grain sample.

7. A combine thresher having a continuous grain moisture analyzer comprising:

a combine thresher having means for moving grain from a grain floor of the combine to a storage bin therein with said moving means being enclosed by an external wall of said combine; and a grain moisture analyzer assembly mounted ex-situ on said external wall of the combine; and means for bypassing a portion of the grain passing through said moving means through said grain moisture analyzer including an inlet opening and an outlet opening formed in said external wall of said combine for supplying and exhausting grain to and from said grain moisture analyzer;

a sensing cell for measuring grain moisture; and feed means for moving the grain from said sensing cell to said outlet opening formed in said external wall for returning said portion of grain back into a normal flow of moving grain within the combine thresher.

* * * * *